United States Patent [19]

Dunbar et al.

[11] Patent Number: 4,701,211

[45] Date of Patent: Oct. 20, 1987

[54] SUBSTITUTED BENZYLTRIETHYLAMMONIUM SALTS AND THEIR USE AS PLANT GROWTH ENHANCERS

[75] Inventors: Joseph E. Dunbar, Midland, Mich.; Theodore W. Holmsen, Clayton, Calif.; Herman O. Senkbeil, Beaverton, Mich.

[73] Assignee: The Dow Chemical Company, Midland, Mich.

[21] Appl. No.: 746,142

[22] Filed: Jun. 18, 1985

Related U.S. Application Data

[63] Continuation of Ser. No. 525,338, Aug. 22, 1983, abandoned, which is a continuation-in-part of Ser. No. 405,674, Aug. 6, 1982, abandoned.

[51] Int. Cl.$^4$ .................... A01N 33/12; C07C 87/30
[52] U.S. Cl. ........................... 71/121; 564/284
[58] Field of Search .................... 564/284, 289; 71/121

[56] References Cited

U.S. PATENT DOCUMENTS

| | | | |
|---|---|---|---|
| 2,689,789 | 9/1954 | Mowry et al. | 564/284 |
| 2,692,264 | 10/1954 | Wojcik | 564/284 |
| 3,037,910 | 6/1962 | Copp et al. | 564/284 |
| 3,280,137 | 10/1966 | Wakeman et al. | 564/284 |
| 3,532,750 | 10/1970 | Crounse et al. | 564/284 |
| 3,671,219 | 6/1972 | Nickell | 71/121 |
| 3,850,611 | 11/1974 | Nakaniski et al. | 71/121 |
| 4,343,647 | 8/1982 | Dunbar et al. | 71/121 |

FOREIGN PATENT DOCUMENTS 924146 4/1964 United Kingdom ............... 564/284

*Primary Examiner*—James H. Reamer
*Attorney, Agent, or Firm*—S. Preston Jones; Ronald G. Brookens

[57] ABSTRACT

Compounds are prepared which correspond to the formula

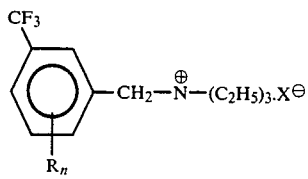

wherein R represents hydrogen, chloro, bromo or trifluoromethyl; n represents an integer of from 1 or 2, with the proviso that when R is trifluoromethyl, n is 1; and X represents a non-phytotoxic anion. The compounds have been found to be active plant growth enhancers.

20 Claims, No Drawings

SUBSTITUTED BENZYLTRIETHYLAMMONIUM SALTS AND THEIR USE AS PLANT GROWTH ENHANCERS

RELATIONSHIP TO PRIOR APPLICATIONS

This is a continuation of application Ser. No. 525,338, filed Aug. 22, 1983, now abandoned, which is a continuation-in-part of application Ser. No. 405,674 filed Aug. 6, 1982 now abandoned.

BACKGROUND OF THE INVENTION

One active area of agricultural research is devoted to the production of more productive plant life, particularly that plant life usually considered as or associated with food sources or beauty for man. In this research, much effort has been expended in developing means for the regulation of the growth pattern of plant life, particularly as evidenced by the retardation of growth and the enhancement of maturation.

These objectives have been accomplished, in part, by the discovery, development and distribution of various chemical agents which alter or modify the growth characteristics of plants. Documentation of such can be found in Dwarfing Plants With Chemicals, Agricultural Research Service, U.S. Dept. of Agriculture, January, 1961.

PRIOR ART

Various ammonium salts have been employed in the control of plant growth. For example, substituted benzyltrialkylammonium salts are taught in Canadian Pat. No. 1,090,799. The compound diethylmethyl(2-phenylalkyl)ammonium iodide is taught in U.S. Pat. No. 3,539,632. Substituted benzyl trialkyl ammonium halides are taught in U.S. Pat. No. 2,772,310. Various quaternary ammonium florides are taught in U.S. Pat. No. 3,277,118.

SUMMARY OF THE INVENTION

The present invention is directed to compounds corresponding to the general formula

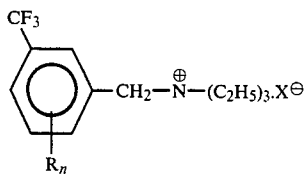

wherein R represents hydrogen, chloro, bromo or trifluoromethyl; n represents an integer of from 1 or 2, with the proviso that when R is trifluoromethyl, n is 1; and X represents a non-phytotoxic anion.

The compounds of the above formula have been found to be active in causing an increase in the growth of various plants. The compounds are particularly effective in altering the growth pattern of many plants such as food crops, ornamental plants and trees.

One of the typical effects of the presently claimed plant growth control agents is an increase in plant size and/or weight.

The substituted benzyltriethylammonium salts of the present invention are crystalline solids or oils, soluble in water and appreciably soluble in common organic solvents.

The specific anion of the salts of the present invention is not critical. The anion can be any of the anions conventionally employed in plant growth regulators. The only limitation upon the anion chosen is that it be non-phytotoxic to the plants being treated. Representative anion include $Cl^{(-)}$, $Br^{(-)}$, $I^{(-)}$, $SCN^{(-)}$, $CH_3CO_2^{(-)}$, $IC_2H_5CO_2^{(-)}$, $\phi SO_3^{(-)}$, $\phi CO_2^{(-)}$, $Cl\text{-}\phi\text{-}O^{(-)}$, $C_3H_7CO_2^{(-)}$, $SO_4^{(=)}$, $PO_4^{(\equiv)}$, $NO_3^{(-)}$, $ClO_3^{(-)}$, and $N_3^{(-)}$, among others.

The compounds of the present invention can be prepared by the reaction of an appropriate substituted (trifluoromethyl)benzylhalide (usually a chloride or bromide) and triethylamine in the presence of a solvent.

The reaction can be characterized as follows:

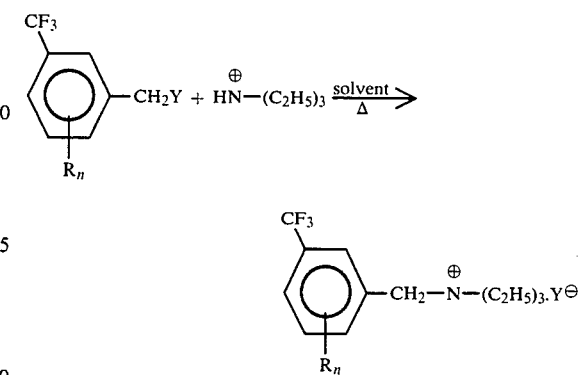

wherein Y is chlorine or bromine.

In carrying out this reaction, the reactants and solvent are mixed together in any suitable fashion and the mixture heated at a temperature in the range of from about 65° to about 150° C. (dependent upon the reactants) and preferably at the reflux temperature of the mixture. The reactants are maintained under such conditions until the reaction is complete. Since the reaction is rather slow, reaction period of from about 2 hours to 1 week or more are not unusual. The specific time period is dependent upon the specific reactants and solvents employed.

The amount of the reactants to be employed is not critical, some of the product being formed when employing any proportions. The reaction, however, consumes the reactants in the ratio of one mole of the benzyl halide per mole of the amine and the employment of such proportions is preferred.

It is preferred to employ polar solvents in carrying out this reaction. Representative solvents include, for example, acetonitrile, butanol, nitromethane and methyl ethyl ketone. When lower boiling solvents are employed, pressures higher than atmospheric may be necessary to permit the use of temperatures higher than the boiling point of the solvent. It is also within the scope of this invention to conduct the reaction in the absence of solvents provided that adequate control is maintained over the temperature.

Upon completion of the reaction, the product is removed from the reaction mixture. This separation can be achieved by (a) removing the solvent by evaporation under reduced pressure and recovering the product as a residue or (b) cooling the reaction mixture and mixing it with a solvent such as, for example, ethyl ether, hexane or mixtures thereof. If the product is solid, it can be separated by filtration or other known solid-liquid separation techniques; if the product is a liquid (oil), it can be separated by decantation or other conventional separation techniques. If desired, solid products can be further purified by recrystallization from solvents such as, for example, methyl ethyl ketone, ethyl acetate, ethyl ether, hexane, ethanol or mixtures thereof. The liquid products can sometimes be crystallized by trituration with the appropriate solvent.

While the above preparative procedures have been described wherein the product is in the form of the chloride or bromide salt (the benzylchloride or bromide having the starting reactant), other salts can be prepared employing conventional procedures.

Such additional salts are prepared by treating the chloride or bromide product at room temperature in water with the alkali or alkaline earth salt of the organic or inorganic acid from which the desired anion is derived. This salt is of the formula $$M^{\oplus} X^{\ominus}$$

wherein M represents the alkali metals such as sodium, potassium, lithium, cesium or rubidium and the alkaline earth metals such as calcium, barium or strontium and X is an hereinabove set forth. These additional salts can also be prepared by passing the product bromide or chloride salt through an ion exchange column charged with the appropriate anion.

DESCRIPTION OF SOME PREFERRED EMBODIMENTS

The following examples illustrate the present invention and the manner by which it can be practical but, as such, should not be construed as limitations upon the overall scope of the same.

EXAMPLE I

Triethyl-(3-(trifluoromethyl)benzyl) ammonium chloride

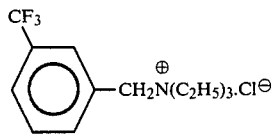

A mixture of 15.3 grams (0.08 mole) of 3-(trifluoromethyl)benzyl chloride and 8.0 grams (0.086 mole) of triethylamine in 50 milliliters of acetonitrile was heated 6 hours at 85° C. The mixture was then stirred over a weekend at room temperature. The crystals which formed were slurried in ethyl ether. The crude product was recovered by filtration and extracted with 600 milliliters of hot methyl ethyl ketone and 0.50 ml of methylene dichloride. The triethyl-(3-trifluoromethyl)benzyl) ammonium chloride was recoved by filtration in a yield of 13.7 grams. The product melted at 213°–215° C. The structure of the compound was confirmed by NMR.

By following the preparative procedures as set forth in the above example and employing the appropriate starting reactants, the following compounds are prepared.

TABLE I

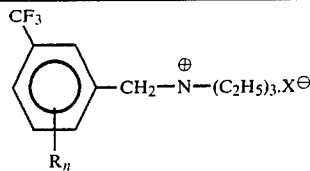

| Compound No. | R | X⁻ |
|---|---|---|
| 2 | H | Br |
| 3 | H | Cl |
| 4 | 4,6-Cl$_2$ | Cl |
| 5 | 4-Cl | Cl |
| 6 | H | $\phi$SO$_3$ |
| 7 | H | NO$_3$ |
| 8 | 6-Br | SO$_4$ |
| 9 | H | CH$_3$CO$_2$ |
| 10 | H | C$_3$H$_7$CO$_2$ |
| 11 | 5-CF$_3$ | $\phi$CO$_2$ |
| 12 | 5-CF$_3$ | Cl |
| 13 | H | SCN |
| 14 | H | 3-Cl$\phi$—O— |
| 15 | H | C$_2$H$_5$CO$_2$ |

It has been discovered that the compounds of the present invention can be employed as plant growth control agents. In this capacity, the compounds of this invention or compositions containing these compounds, as the active ingredient are useful in enhancing the growth of plants. The plants after treatment exhibit an increased growth and/or longer or more fruit and increased plant weight.

The compounds can be applied directly to the plant itself, i.e., above-ground surfaces of the plants, seeds, roots or tubers and the like.

The exposure of viable plants and plant parts to the action of a growth regulating amount of the compounds of the present invention is essential and critical for the practice of the present invention. The exact dosage to be employed, is not the same for all plants with all compounds and is dependent upon the response desired in the plant as well as such other factors as the plant species and the stage of growth at which treatment is made, and climatic conditions such as temperature, wind and especially rainfall.

In foliar treatments for the enhancement of the growth of germinant seeds, emerging seedlings and established vegetation good results are obtained when from 0.002 pound to 5.0 pounds, preferably 0.01 to 2 pounds of the compounds are applied per acre.

The method of the present invention can be practiced by distributing the unmodified compounds upon the surfaces of the above-ground portion of plants. However, the present method also embraces the similar employment of liquid or dust compositions containing the compounds. In such usages, the compounds can be modified with one or a plurality of additaments or adjuvants including water or other liquid carriers, surface-active dispersing agents, and finely-divided solids. Depending upon the concentration of the compounds, such augmented compositions are adapted to be distributed upon the above-ground surfaces of plants, or to be employed as concentrates and subsequently diluted with additional inert carrier to produce the ultimate treating compositions. In compositions where the adjuvant or helper is a finely-divided solid, a surface-active agent or the combination of a surface-active agent and a finely divided solid, and/or a liquid additament, the adjuvant and/or adjuvants cooperate with the compounds so as to facilitate the invention and obtain an improved and outstanding result.

As indicated above, the compound can be directly applied to seeds prior to planting. The application to seeds of an effective growth enhancing dosage of the active compounds is essential and critical for the practice of the present invention. Good results are obtained when the seeds are treated with the compounds at a dosage of from about 0.0001 pound per hundred pounds of seed up to the phytotoxic threshold. The latter is about 0.1 pound per hundred pounds of seed inasmuch as lasting phytotoxic effects are obtaining with many plants at dosage levels above the 0.1 pound level. Depending on the particular plant species and variety and on the growing conditions some undesirable phytotoxic effects may be encountered even below the 0.1 pound level. Within the above set forth treating range, the maximum growth enhancement response is obtained, and any phytotoxicity experienced in the very early stages of plant growth is usually overcome as the plant begins the growth and maturation habit which is characterized by the present process.

The treatment of the seeds may be accomplished by shaking or otherwise contacting the seeds with a dust composition containing the active agent, or by wetting the seeds with a liquid composition. In a convenient method of application, the compositions are applied in the form of dusts or sprays to the seeds as the latter are transported on the surface of a slowly moving belt or a perforated material such as a wire screen. In still another method, the required dosage of active agent can be applied on and about the seeds by the seed planting implement either in the hopper box or as the seeds are being planted into the soil or other growth media.

The exact concentration of the compounds to be employed in the treating compositions is not critical and may vary considerably provided the required dosage of the compounds is supplied upon the plant foliage. The concentration of the compound in liquid compositions employed to supply the desired dosage generally is from about 0.001 to 50 percent by weight although concentrations as low as 0.0001 percent and as high as 90 percent by weight are sometimes advantageously employed. In dusts, the concentration of toxicant is from about 0.1 to 90 percent by weight and usually not in excess of about 20 percent. In both liquid and dust compositions to be employed as concentrates, the compounds can be present in a concentration of from 5 to 98 percent by weight.

The quantity of treating compositions to be applied can vary considerably provided that the required dosage of the compound or active ingredient is applied in a sufficient amount of the finished composition to cover adequately the vegetation to be treated. In the treatment of seedlings good coverage is obtained when using from 1 to 60 gallons of finished spray composition per acre. Where large plants are concerned, it is frequently desirable to employ up to 600 gallons or more of the finished spray composition per acre to assure complete coverage of the above-ground portion of the vegetation. In the application of dusts to plant foliage, good results are obtained with from 40 to 2,000 pounds of finished dust per acre, the only requirement being that the required toxicant dosage be supplied in sufficient dust to achieve good coverage of the foliage.

Liquid compositions containing the desired amount of active ingredient can be prepared by dispersing the compounds in water or in organic liquid, with or without the aid of a suitable surface-active dispersing agent such as an ionic or non-ionic emulsifying agent. Suitable organic liquid carriers include the agricultural spray oils and the petroleum distillates such as diesel fuel, kerosene, fuel oil, and naphthas. The organic liquid compositions can contain a small amount of water as a solvent for the active ingredient. In such compositions, the carrier comprises an emulsion, namely, a mixture of water, emulsifying agent and organic liquid. In the liquid compositions, the choice of dispersing and emulsifying agent and the amount thereof employed is dictated by the nature of the composition and by the ability of the agent to facilitate the dispersion of the compounds in the carrier to produce the desired composition or to facilitate the wetting of surfaces upon which the compositions are applied. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, mahogany soaps and the like.

In the preparation of dust compositions, the active ingredient is dispersed in and on a finely-divided solid such as clay, talc, chalk, gypsum, sugar, salt, bicarbonate, fertilizer and the like. In such operations, the finely-divided carrier is mechanically mixed or ground with the compounds. Similarly, dust compositions containing the compounds can be prepared from various of the solid surface-active dispersing agents such as bentonite, fuller's earth, attapulgite and other clays. Depending upon the proportion of ingredients, these dust compositions can be employed as concentrates and subsequently diluted with additional solid surface-active dispersing agent or with chalk, talc or gypsum, sugar, salt, fertilizer, and the like to obtain the desired amount of active ingredient in a composition adapted to be employed for the modification of the growth of plants. Also such dust compositions can be dispersed in water with or without the aid of a dispersing agent to form spray mixtures.

When operating in accordance with the present invention, growth enhancing amounts of the compounds are dispersed in any convenient fashion. The application of spray and dust compositions to the above-ground surfaces of plants can be carried out by conventional methods, e.g., power dusters, boom and hand sprayers and spray dusters.

The expression "surface-active dispersing agent" as herein employed is intended to include all agents which are capable of acting at the interfacial surface as the dispersion medium. Thus, the term is inclusive of the solid emulsifying agents such as finely-divided aluminum hydroxide and finely-divided bentonite, fuller's earth, attapulgite and other clays, as well as the ionic and non-ionic wetting and emulsifying agents such as the alkaline earth metal caseinates, alkyl aryl sulfonates, sulfonated oils, complex organic ester derivatives, complex ether alcohols, and the like.

The finely-divided inert solid or carrier as herein described refers to materials which are incapable of facilitating dispersion but which serve as a distribution medium for the active compounds. They include finely-divided materials such as chalk, talc, gypsum, sugar, salt, bicarbonate, fertilizers, and so forth.

EXAMPLE II

Tests were conducted to determine the effectiveness of triethyl-(3-(trifluoromethyl)benzyl)ammonium chloride in increasing the rate of photosynthesis as evidenced by an increase in the dry weight of the roots of sugar beets.

Sugar beets were grown in a greenhouse in pots whose soil consisted of ~97 percent sand. When the plants were about 21 days old, they were sprayed to the point of run-off with various dilutions of aqueous solutions of triethyl-(3-(trifluoromethyl)benzyl)ammonium chloride. These solutions were prepared by dissolving a predetermined amount of the compound in a predetermined amount of water containing 0.1 percent of a wetting agent. Untreated plants were maintained as controls.

One month after treatment, the plants were removed from the soil and the roots removed from the plants. The roots were placed in a forced air oven at 60° C. until no moisture remained (48–72 hours). The dry weight of the roots were measured and the results calculated as a percent of the control.

TABLE II

| Concentration of Triethyl-(3-(trifluoromethyl)benzyl)-ammonium chloride in ppm | Dry weight of sugar beet roots as percent of control |
| --- | --- |
| 5.0 | 38% |
| 10.0 | 22% |
| 25.0 | 30% |

EXAMPLE III

Tests were conducted to determine the effectiveness of triethyl-(3-(trifluoromethyl)benzyl)ammonium chloride in increasing the weight and the sugar content of sugar beets.

Sugar beets grown from seed were sprayed 8 weeks after planting with various dilutions of aqueous solutions of the above indicated compound. These solutions were prepared by dissolving a predetermined amount of the compound in a predetermined amount of water containing 0.1% of a wetting agent. The plants were sprayed at a rate equivalent to 20 gallons of the solution per acre.

Two weeks after treatment, photosynthesis was estimated on an intact plant using $^{14}CO_2$ fixation for a 30-second exposure of a leaf in a plastic chamber.

The sugar content of the beet was estimated by measuring the refractive index of juice expressed from frozen and thawed plugs of root tissue. Sugar content was measured at both 5 and 14 weeks after treatment.

The weight of the beet root was also measured 5 weeks after treatment.

Untreated plants were maintained as controls.

The results of the above testing is as follows:

TABLE III

| Chemical | Treating rate in ounces per acre | Photosynthesis as percent of control | Fresh weight in grams of beet roots | Sugar content of beets 5 weeks after Treatment | Sugar content of beets 14 weeks after Treatment |
| --- | --- | --- | --- | --- | --- |
| Triethyl-(3-(trifluoromethyl)benzyl)ammonium chloride | 0.5 | 151 | 335 | 14.4 | @ |
|  | 1.5 | 77 | 448 | 14.6 | @ |
|  | 4.5 | 154 | 628 | 15.4 | 16.2 |
| Control | 0 | 100 | 432 | 14.7 | 15.4 |

@ = value not determined.

Example IV

Tests were conducted to determine the effectiveness of triethyl-(3-(trifluoromethyl)benzyl)ammonium chloride in increasing the weight and the sugar content of sugar beets.

Sugar beets grown in plots from seed were sprayed 19 weeks after planting with various dilutions of aqueous solutions of the above-indicated compound. These solutions were prepared by dissolving a predetermined amount of the compound in a predetermined amount of water containing 0.1% of a wetting agent. The plants were sprayed at a rate equivalent to 20 gallons of the solution per acre.

Six weeks after treatment the following measurements were made.

The sugar content of the beet was estimated by measuring the refractive index of juice expressed from frozen and thawed plugs of root tissue.

The weight of the beet root was also measured. The plants were harvested at this time and processed in the normal commercial way.

Untreated plants were maintained as controls.

The results of the above measurements is as follows:

TABLE IV

| Compound | Treating rate in ounces per acre | Average weight per beet root in pounds | Percent sugar in beet roots | Pounds of sugar on per plot basis |
| --- | --- | --- | --- | --- |
| Triethyl-(3-(trifluoromethyl)-benzyl)ammonium chloride | 0.5 | 2.61 | 11.9 | 14.2 |
|  | 1.5 | 2.60 | 12.5 | 14.9 |
|  | 4.5 | 2.48 | 12.2 | 13.0 |
| Control | 0 | 2.33 | 11.8 | 12.9 |

EXAMPLE V

Tests were conducted to determine the effectiveness of triethyl-(3-(trifluoromethyl)benzyl)ammonium chloride in increasing the growth of silver maple trees.

Seedlings from silver maple trees which had been kept in cold storage, were planted in 97% sand and placed in a greenhouse to bud. The trees after planting were trimmed to only one growing point and allowed to develop four fully expanded leaves. The plants were sprayed to run-off with aqueous spray compositions which had been prepared by dissolving a predetermined amount of the active compound in a predetermined amount of a water-surfactant mixture to give aqueous dispersions containing varying amounts of the active compound. Untreated plants were maintained as controls.

One month after treatment, stem growth which occurred after treatment was measured. That amount of stem plus the leaves were then placed in an oven at 60° C. for 48 hours. At the end of which time, the dry weight was measured. Growth and dry weight were calculated as a percent of control. It was found that at a treatment rate of 125 ppm, a 23% increase in dry weight occurred along with a 6% increase in growth. At the higher rate of 250 ppm, no activity was observed for the compound. At the further higher rate of 500 ppm a 14% increase in dry weight occurred with no increase in growth.

EXAMPLE VI

Tests were conducted to determine the effectiveness of triethyl-(3-(trifluoromethyl)benzyl)ammonium chloride in increasing the leaf area and the dry weight of tobacco plants.

Tobacco seeds were planted in vermiculite and grown in a greenhouse in pots. When the plants were about 21 days old, they were sprayed to the point of run-off with various dilutions of aqueous solutions of triethyl-(3-(trifluoromethyl)benzyl)ammonium chloride. These solutions were prepared by dissolving a predetermined amount of water containing 0.1 percent of a wetting agent. Untreated plants were maintained as controls.

Fourteen days after treatment, leaf area was measured by using a Li-Cor area meter. The leaves were then removed from the plants and placed in an oven at 60° C. for 48 hours and the dry weight of the leaves were measured. Leaf area and dry weight were calculated as a percent of control. It was found that at a treatment dosage of 12.5 ppm, the leaf area was increased about 12% with a dry weight increase of 13%. At a treatment dosage of 50 ppm, the leaf area increased 7% and the dry weight increased 11%.

What is claimed is:

1. A compound corresponding to the formula

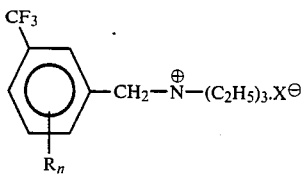

wherein R represents hydrogen or trifluoromethyl; n represents an integer of from 1 or 2, with the proviso that when R is trifluoromethyl, n is 1; and X represents a non-phytotoxic anion.

2. A compound as defined in claim 1 wherein R is hydrogen.

3. A compound as defined in claim 1 wherein R and n is 1.

4. A compound as defined in claim 1 wherein R and n is 2.

5. The compound as defined in claim 2 which is triethyl-(3-(trifluoromethyl)benzyl)ammonium chloride.

6. A composition useful for treating plants to increase the growth of said plants which contains as the active material, an effective plant growth regulating amount of a compound corresponding to the formula

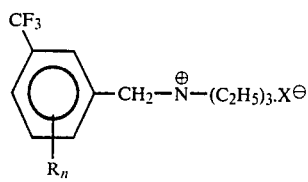

wherein R represents hydrogen or trifluoromethyl; n represents an integer of from 1 or 2, with the proviso that when R is trifluoromethyl, n is 1; and X represents a non-phytotoxic anion in admixture with an inert carrier therefor.

7. A composition as defined in claim 6 wherein R is hydrogen.

8. A composition as defined in claim 6 wherein n is 1.

9. A composition as defined in claim 6 wherein n is 2.

10. The composition as defined in claim 7 wherein the active material is triethyl-(3-(trifluoromethyl)benzyl)ammonium chloride.

11. The composition as defined in claim 6 in which the active material is present in the amount of from 0.0001 to 90 percent by weight of the ultimate composition.

12. A method for enhancing the growth of plants to obtain an increase in weight or size of said plants which comprises contacting plants or plant parts or their habitat with a growth enhancing amount of a composition containing as the active material a compound corresponding to the formula

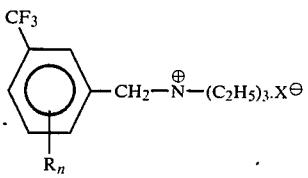

wherein R represents hydrogen or trifluoromethyl; n represents an integer of from 1 or 2, with the proviso that when R is trifluoromethyl, n is 1; and X represents a non-phytotoxic anion in admixture with an inert carrier therefor.

13. The method as defined in claim 12 wherein R is hydrogen.

14. The method as defined in claim 12 wherein n is 1.

15. The method as defined in claim 12 wherein n is 2.

16. The method as defined in claim 13 wherein the active material is triethyl-(3-(trifluoromethyl)benzyl)ammonium chloride.

17. The method as defined in claim 12 in which plant seeds are contacted.

18. The method as defined in claim 12 in which the above-ground portions of the plants are contacted.

19. The method as defined in claim 17 wherein the seeds are contacted with from 0.0001 to 0.1 pound of the active material per 100 pounds of seed.

20. The method as defined in claim 18 wherein the above-ground portions of the plants are contacted with from 0.002 pound to 5.0 pounds of the active material per acre.

* * * * *